United States Patent
Zohoungbogbo

(12) 
(10) Patent No.: US 6,322,826 B2
(45) Date of Patent: *Nov. 27, 2001

(54) DIETETIC FOOD COMPOSITION AND DIETETIC METHOD USING SUCH COMPOSITION

(75) Inventor: Mathias Christian Zohoungbogbo, ViaGorizia, 43 - 10040 Rivalta di Torino (IT)

(73) Assignee: Mathias Christian Zohoungbogbo, Turin (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/333,097

(22) Filed: Jun. 15, 1999

Related U.S. Application Data

(63) Continuation-in-part of application No. 09/225,819, filed on Jan. 5, 1999, now abandoned.

(30) Foreign Application Priority Data

Jun. 16, 1998 (EP) .................................................. 98830365
Jun. 4, 1999 (EP) .................................................. 99201794

(51) Int. Cl.$^7$ ..................................................... A23K 1/00
(52) U.S. Cl. ........................... 426/2; 426/549; 426/601; 426/804; 514/386; 514/561
(58) Field of Search ............................ 426/549, 2, 804, 426/601; 514/386, 561

(56) References Cited

U.S. PATENT DOCUMENTS

| | | | | |
|---|---|---|---|---|
| 4,830,861 | * | 5/1989 | Pusk et al. | 426/18 |
| 4,961,937 | * | 10/1990 | Rudel | 426/19 |
| 4,966,778 | * | 10/1990 | Benjamin et al. | 426/19 |
| 4,990,344 | * | 2/1991 | Euber et al. | 426/26 |
| 5,106,634 | | 4/1992 | Thacker et al. | 426/31 |
| 5,484,623 | * | 1/1996 | McLean | 426/601 |
| 5,595,772 | * | 1/1997 | Wurtman et al. | 426/2 |
| 5,698,256 | * | 12/1997 | Stilling | 426/656 |
| 5,817,695 | * | 10/1998 | Pellico | 514/558 |

FOREIGN PATENT DOCUMENTS 1508940  4/1978 (GB) .............................. A21D/2/00

OTHER PUBLICATIONS

European Search Report, Dec. 18, 1998.

* cited by examiner

*Primary Examiner*—Nina Bhat
(74) *Attorney, Agent, or Firm*—Sofer & Haroun, LLP

(57) ABSTRACT

Food composition in the form of a flour comprising at least 50% of protein, less than 15% of carbohydrates and 35 to 50% of plant fibers; preferably the carbohydrate content is less than 10%, advantageously less than 5%; this composition may be used as a substitute for wheat flour in the preparation of foods such as pasta, bread, bread sticks, bakery products and pastries and constitutes the basis of a method for improving the appearance of a person by achieving a loss of weight which is beneficial from the aesthetic point of view.

38 Claims, No Drawings

DIETETIC FOOD COMPOSITION AND DIETETIC METHOD USING SUCH COMPOSITION

RELATED DATA

This application is a continuation-in-part of U.S. application Ser. No. 09/225,819 filed on Jan. 5, 1999, abandoned which in turn claims the benefit of earlier filed foreign patent applications, namely European Patent Application No. 98830365.7 filed on Jun. 16, 1998 at the Italian Patent Office and European Patent Application No. 99201794.7 filed on Jun. 4, 1999 at the European Patent Office of the Hague.

FIELD OF THE INVENTION

This invention relates to the sector of the food and dietetic industry.

In particular, the invention relates to a substitute food composition for cereal flours in general and for wheat flour in particular, and foods which can be prepared using this composition.

The invention also relates to a method for controlling the body weight of an individual.

BACKGROUND ART

It is well known that in the developed nations and even in the developing nations the percentage of individuals having excess weight if not obesity problems is constantly and progressively increasing. This has important consequences both for the health of individuals and for the overall health cost of the various nations, because it has been amply demonstrated that obesity or even being overweight are important associated causes of cardiovascular and metabolic diseases, such as myocardial infarction, stroke, type II diabetes, etc.

The dietetic measures generally proposed by dieticians to combat and/or prevent excess weight mainly consist of low-calorie or low-fat regimes.

Another widely recommended measure for the control of body weight which is even advocated by the mass media (periodicals, television, etc.) is adoption of the famous "Mediterranean diet", based on foods rich in complex carbohydrates such as pasta, rice, bread and the like.

It is, however, a fact that the widespread use of low-calorie diets and the Mediterranean diet has not in fact resulted in any statistically significant change in the percentage of obese or overweight persons; there is instead a progressive increase in this percentage.

A low-calorie diet can in fact have some temporary effect on reducing body weight but this cannot be maintained for a long period, either because it results in general weakening of the body, or because over the long term it is rejected by the individual because of the monotony of the flavours of the food making it up (essentially meat, fish and greens).

The so-called "Mediterranean diet" is in fact only suitable for maintaining the right weight and the right form in individuals who are engaged in vigorous physical activity. Persons who are engaged in essentially sedentary work can on the other hand experience an increase in weight and an accumulation of lipids when they feed themselves on foods based essentially on carbohydrates.

SUMMARY OF THE INVENTION

The problem underlying this invention is that of providing a diet/foodstuff which allows obese or merely overweight persons to recover their ideal weight by eliminating excess lipids and to maintain such an ideal weight over a long period of time. All this without the persons having to subject themselves to a low-calorie diet and to suffer the deprivation of foodstuffs which it is difficult to do without over long periods, such as pasta, bread and bakery products in general.

Such a problem is solved according to the invention by a food composition in the form of a flour comprising at least 50% of protein, up to 15% of carbohydrates and from 35 to 50% of plant fibres.

The diet according to the present invention is characterized by totally or partially eliminating carbohydrates from overweight persons' diet. Said kind of diet is usually known in the art as ketogenic diet. The ketogenic diet satisfies always one's appetite and brings always to a loss in weight, but may also cause several side-effects such as, for instance, hyperuricemia, hyperglycemia, hypercholesterolemia, hypertriglyceridemia, hepatic-pancreatic alterations, mental disorders, etc.

Therefore, a further problem underlying this invention is that of providing a composition for preventing and treating the above mentioned side-effects which can occur in a ketogenic diet such as the one according to the present invention.

Said further problem is solved by a pharmaceutical composition as recited in the appended claims.

DETAILED DESCRIPTION OF THE INVENTION

The present invention relates to a food composition in the form of a flour. The carbohydrate content of the food composition according to the present invention is preferably less than 10%, advantageously less than 5%.

The proteins are preferably selected from the group comprising gluten, soya proteins, milk proteins in particular from soya milk without lactose, animal proteins obtained from meat or dried or smoked fish, egg albumen and yolk, wheat proteins, wheat germ, rice germ, soya bean protein, pea protein.

The plant fibres are preferably selected from the group comprising cereal fibres, in particular wheat, maize and oats, wheat, maize and soya bean brands, vegetable fibres, in particular tomato, spinach, inulin, acacia and fruit fibres, in particular oranges and apples.

The food composition according to the present invention may additionally comprise vegetal fat, in particular from coconut and soya bean and animal lipids, in particular from yolk, cream and whole milk.

Said food composition may further comprise flours, in particular flours selected from the group consisting of tender wheat flour and drum wheat flour.

Both the proteins and the plant fibres are used in a finely divided form and mixed in suitable ratios to produce flours which can be used as substitutes for wheat flour in the preparation of foods such as pasta, bread, bread sticks, bakery products and pastries.

This invention also relates to a method for improving the appearance of a person by achieving a loss of weight which is beneficial from the aesthetic point of view, this method comprising the elimination from the said person's diet of all carbohydrate-based foods and their replacement with foods obtained using the flours described above.

Advantageously such a method provides for the initial use of flours having the lowest carbohydrate content possible, in any event a content of not more than 5% by weight.

A certain although minimum carbohydrate content is always present in the flours according to the invention because commercially available plant fibres always have a small residual glucide content. Once the desired aesthetic effects have been achieved, it is then possible, according to the method of the invention, to use flours with a higher carbohydrate content in a second stage. Preferably flours with a carbohydrate content up to 15% should be used.

In a third stage of the method, which can be described as a maintenance stage, the carbohydrate content of the flours can be further increased, without however exceeding the threshold of 20% by weight. This guarantees maintenance of the aesthetic effects obtained, while at the same time introducing greater variety into the diet.

In addition, the effect of the above diet can be improved by means of a combination with adjuvants for the treatment of obesity. Said adjuvants comprise at least one adjuvant selected from the group consisting of sedative-ansiolytic agents, anorectic agents and lipolytic agents.

The sedative-ansiolytic agent is preferably a benzodiazepine, most preferably 7-chloro-2,3-dihydro-2-oxo-5-phenyl-1H-1,4-benzodiazepine (dipotassium chlorazepate). A preferred dosage of the dipotassium chlorazepate is from 0.5 mg to 10 mg per day for an adult of a weight of about 70 kg.

The anorectic agent is preferably selected from the group consisting of 1-phenyl-2-diethylamine-1-proparone hydrochloride (diethylpropione chlorohydrate), fenfluramine chlorohydrate and D-fenfluramine chlorohydrate. A preferred dosage of the anorectic agent is from 2 mg to 35 mg per day for an adult of a weight of about 70 kg.

The lipolytic agent is preferably selected from the group consisting of analogues of tiroxine, most preferably said agent is 3,5,3'triiodiotiroacetic acid. A preferred dosage of the lipolytic agent is from 0.2 mg to 0.8 mg per day for an adult of a weight of about 70 kg.

The method according to the invention therefore provides for an individual who intends to lose weight to eliminate all carbohydrate-rich foods such as bread, pasta, sweets and bakery products in general from his diet and to replace them by "facsimile" foods obtained using the flours described above, using non-sugar sweeteners in the case of sweets.

The above-mentioned flours may be used in the same way as wheat flour. To prepare bread for example, such flours are made into a dough with water and yeast, and possibly salt, lard, olive oil or other optional ingredients, allowed to rise and then baked in an oven at the same temperature at which bread is baked.

Similarly, in order to prepare sweets such as tarts, biscuits or the like, the flours are made into a dough with butter or margarine or similar fats, eggs, yeast if desired and other optional ingredients, with the addition of non-glucide sweeteners (e.g. saccharine) and baked in an oven in the same way as traditional sweets.

Those who intend to retain their ideal weight by following the method according to the invention should also abstain from consuming fruits which are rich in sugars, sweetened drinks, etc.

As said above, a pharmaceutical composition is also provided for preventing or treating the side-effects which can occur in a ketogenic diet.

In particular, said pharmaceutical composition A comprises an hypocholesterolemic agent, a hypotriglyceridemic agent, a lipasic and proteasic agent, a hypoglycemic agent and a hydrocoleretic agent.

The hypocholesterolemic agent is preferably selected from the group consisting of 2-[alpha-methyl-(trifluoromethyl)phenethylamine]-ethanolbenzoate (benfluorex) and 3-alpha-7B-dihydroxy-5B-colan-24 oic acid (ursodesoxycolic acid).

The hypotriglyceridic agent is preferably 2-[alpha-methyl-(trifluoromethyl)phenethylamine]-ethanolbenzoate (benfluorex) which is preferably present in a global amount from 7% to 23% in weight with respect of the total amount of the composition A.

The lipase and protease agent is preferably total lyophilized pancreas (Pancreatine IX F.U.) which is preferably present in an amount from 27% to 43% in weight with respect of the total amount of the composition A.

The hypoglycemic agent is preferably selected from the group consisting of biguanides, said biguanides being preferably 1,1-dimethylbiguanide (metformine) which is preferably present in an amount from 36% to 41% in weight with respect to the total amount of the composition A.

The hydrocoleretic agent is preferably selected from the group consisting of 3,7,12-triose-5B-colan-24 oic acid (Na dehydrocolate) and 3alfa-7B-dihydroxy-5B-colan-24 oic acid (ursodesoxycolic acid). When Na dehydrocolate is present, it is preferably in an amount from 9% to 14% in weight with respect of the total amount of the composition A. When ursodesoxycolic acid is present, it is preferably in an amount from 14% to 17% in weight with respect to the total amount of the composition A.

The composition may additionally comprise an hypouricemic agent. Said agent is preferably centella asiatica purified triterpenes which may be preferably present in a ratio from 0.04:1 to 0.5:1 in weight with respect to the total amount of the composition A.

Moreover, the composition may comprise a radical scavenger agent. Preferably said agent is selenium which may be preferably present in a ratio from 0.0001:1 to 0.0003:1 in weight with respect to the total amount of the composition A.

The composition may also comprise a sympatholytic agent. Said agent is preferably methyl 17-alfa-hydroxy-yohimbane-16-alfa-carboxylate (yohimbine) which may be preferably present in a ratio from 0.0009:1 to 0.007:1 in weight with respect of the total amount of the composition A.

The composition may additionally comprise a sympathicomimetic agent. Said agent is selected from the group consisting of phendimetrazine bitartrate and phendimetrazine pamoate, which may be preferably present in a ratio from 0.004:1 to 0.1:1 in weight with respect to the total amount of the composition A.

Furthermore, the composition may comprise at least one vitamin, preferably said at least one vitamin is selected in the group consisting of vitamin A, vitamin $B_1$, vitamin $B_6$, vitamin E and vitamin C.

When vitamin A is present, it is in a ratio from 0.4:1 to 1.8:1 in weight with respect to the total amount of the composition A.

When vitamin $B_1$ is present, it is in a ratio from 0.002:1 to 0.007:1 in weight with respect to the total amount of the composition A.

When vitamin $B_6$ is present, it is in a ratio from 0.04:1 to 0.2:1 in weight with respect to the total amount of the composition A.

When vitamin E is present, it is in a ratio from 0.09:1 to 1:1 in weight with respect to the total amount of the composition A.

When vitamin C is present, it is in a ratio from 0.09:1 to 0.3:1 in weight with respect to the total amount of the composition A.

The composition A may further comprise at least one adjuvant selected from the group consisting of a sedative-ansiolytic agent, an anorectic agent and a lipolytic agent.

The sedative-ansiolytic agent is preferably a benzodiazepine, most preferably 7-chloro-2,3-dihydro-2-oxo-5-phenyl-1H-1,4-benzodiazepine (dipotassium chlorazepate) which is preferably present in a ratio from 0.0004:1 to 0.03:1 in weight with respect to the total amount of the composition A.

The anorectic agent is preferably selected from the group consisting of 1-phenyl-2-diethylamine-1-proparone hydrochloride (diethylpropione chlorohydrate), fenfluramine chlorohydrate, D-fenfluramine chlorohydrate. Said anorectic agent is preferably present in an amount from 0.002:1 to 0.1:1 in weight with respect to the total amount of the composition A.

The lipolytic agent is preferably selected from the group consisting of analogues of tiroxine, most preferably said agent is 3,5,3'triiodiotiroacetic acid which is preferably present in a ratio from 0.0002:1 to 0.003:1 in weight with respect to the total amount of the composition A.

All the above agents which can be comprised into the composition A, are usually commercially available.

In particular, diethylpropione chlorohydrate is an anorectic agent used as adjuvant in the treatment of obesity. It shows the same activity of the amphetamine, but with less effects upon the CNS (Central Nervous System) and upon cardiovascular system. Therefore, it is preferable for hypertensive, cardiopath, diabetic and elderly persons.

Fenfluramine and D-fenfluramine are anorectic agents used as adjuvants in the treatment of obesity, which show a psycho-stimulating effect.

Benfluorex is an hypocholesterolemic and hypotriglyceridemic agent which also shows anorectic and hypoglycemic activities.

Centella asiatic is a light diuretic, antirheumatic and peripheral vasodilative agent used in the treatment of the pre-varicose status.

Pancreatine IX F.U. is total lyophilized pancreas used in the treatment of pancreatic insufficiency.

Metformine is an hypoglycemic agent used in the treatment of diabetes specially if in the presence of obesity. It has been also demonstrated a positive effect of metformine on lipid metabolism and on decrease in weight as well as an anorectic activity on diabetic obese patients.

Na dehydrocolate is an hydrocoleretic agent which causes the low-density biliary secretion.

Ursodesoxycolic acid is an agent used to fluidify the bile. It has an anti-cholesterol activity, too.

Selenium is an element used as radical scavenger. It is also used to prevent Kershan disease and as adjuvant during chemotherapy.

Yohimbine is a sympatholytic agent as well as a mydriatic agent. It has been used in the treatment of impotence.

Vitamin A is used to cure hypovitaminosis, malabsorption, malnutrition and to treat dermatological diseases.

Vitamin $B_1$ is used in the treatment and prophylaxis of thiamine deficit, in the treatment of gravidic hyperemesis, neuritis caused by pellagra and during pregnancy.

Vitamin $B_6$ is used in the treatment and prophylaxis of pyridoxine deficit, in the treatment of anaemia, convulsions, gravidic and radiant hyperemesis in the prophylaxis of peripheral neuritis.

Vitamin E is used to cure hypovitaminosis, lipid malabsorption and is used as anti-oxidant for premature infants.

Vitamin C is used to treat ascorbic acid deficit.

Triiodiotiroacetic acid is a thyroid hormone which shows a lipolytic activity.

Dipotassium chlorazepate is a sedative-ansiolytic agent which has the pharmacological activity of the benzodiazepine.

Fendimetrazine bitartrate and pamoate are sympathomimetic agent. They also shows a central anorectic activity.

The composition of the drug and the doses will vary with the conditions of the patients to be treated. Therefore, specific dosages regiments should be adjusted to the individual need and the professional judgement of the person administering or supervising the administration of the aforesaid composition. The dosages may be administered at once or may be divided into a number of smaller doses to be administered at varying intervals of time.

Said agents have been selected to be combined in a synergetic way such that to improve their single pharmaceutical properties and, at the same time, not interfering one with the others.

The advantage provided by said pharmaceutical composition is that of preventing or treating the above mentioned side-effects which can occur in a diet lacking in carbohydrates.

Moreover, by means of a combination of the food composition and of the pharmaceutical composition according to the invention, it is always possible to loose weight without the person having to suffer deprivation of foodstuffs such as pasta, bread and bakery product.

The pharmaceutical composition of the invention may additionally contain excipient and optionally other auxiliary agents, if necessary.

The composition of the present invention can be administered in different pharmaceutical formulation, the precise nature of which will depend upon the chosen route of administration.

Thus, solid compositions for orally administration include compressed tablets, dispersible powders, granules and capsules.

In tablets, the active components are admixed with at least one inert diluent such as lactose, starch, mannitol, microcrystalline cellulose or calcium phosphate; granulating and disintegrating agents for examples corn starch, gelatine, microcrystalline cellulose or polyvinylpyrrolidone; lubricating agents such as magnesium stearate, stearic acid or talc. The tablets may be coated by known techniques to delay disintegration and absorption in the gastrointestinal tract and, thereby, provide a sustained action over a long period. Gastric film-coated or enteric film-coated can be made with sugar, gelatin, hydroxypropylcellulose or acrylic resins.

Formulation for oral use may also be presented as hard capsules of absorbable material, such as gelatin, wherein the active ingredient is mixed with an inert diluent and lubricating agents, or pasty materials, such as ethoxylated saturated glycerides.

Soft gelatine capsules are possible wherein the active ingredient is mixed with water or an oil medium, for example, peanut oil, liquid paraffin or olive oil.

Dispersible powders and granules suitable for preparation of a suspension by the addition of water provide the active ingredient in admixture with dispersing or wetting agent, a suspending agent, such as sodium carboxymethylcellulose, sodium alginate, polyvinylpirrolidone, gum tragacanth, xantham gum, gum acacia and one or more preservatives, such as methyl or n-propyl-p-hydroxybenzoate. Additional excipients, for example sweetening, flavouring and colouring agents may also be present.

Liquid composition for oral administration include emulsions, solutions, suspensions, syrups and elixirs containing commonly used inert diluents, such as distilled water, ethanol, sorbitol, glycerol or propylene glycol. Such compositions may comprise adjuvants such as wetting agents, suspending agents, sweetening, flavouring, perfuming, preserving agents and buffers.

The pharmaceutical composition of the present invention may also be administered in the form of suppositories for rectal administration of the drug.

The dosage and frequency of dose may vary depending upon symptoms, age and body weight of the patient, as well as upon the route of administration, but in general the composition of the present invention may be administered orally in doses of from 7 g to 23 g a day to a patient of the average weight of 70 kg.

The above composition may be prepared in the form of a kit. Said kit may comprise the composition as such or its components separately prepared, for instance, in the form of different capsules. In this manner it is possible to combine different compounds and/or their different amount depending on the patient to be treated.

It is therefore a further object of the present invention a kit of parts for sequential, simultaneous or separate administration as recited in the appended claims.

The food composition, the method and the pharmaceutical composition according to this invention will be further described with reference to the examples provided below merely by way of non-restrictive illustration in which the percentages stated are to be understood as percentages by weight of the total dry weight.

EXAMPLE 1

| Wheat gluten | 55% |
|---|---|
| Wheat fibre | 40% |
| Vegetable fibres | 5% |

By wheat fibre is meant the fibre of the wheat stems (one example of a commercially available product is that sold by the name of VITACEL®).

Wheat gluten is a product marketed by various firms such as for example the company Rocchetta (Italy).

The vegetable fibres are for example fibres of tomato, spinach, onion, etc.; these fibres are marketed by various firms, including Newfood (Italia).

EXAMPLE 2

| Wheat gluten | 35% |
|---|---|
| Soya proteins | 20% |
| Wheat fibre | 45% |

An example of a commercially available product comprising soya protein is Soymino.

EXAMPLE 3

| Wheat gluten | 35% |
|---|---|
| Fruit fibres | 45% |
| Soya proteins | 20% |

The fruit fibres used in this composition were those marketed in Italy under the name VITACEL Arancia® and VITACEL Mela®.

EXAMPLE 4

| Wheat gluten | 34% |
|---|---|
| Wheat germ | 33% |
| Wheat fibre | 17% |
| Vegetable fibres | 16% |

Wheat germ is marketed by various producers, such as for example the company Rizzolio (Italy).

EXAMPLE 5

| Milk proteins | 10% |
|---|---|
| Wheat fibre | 15% |
| Wheat germ | 60% |
| Fruit fibres | 15% |

EXAMPLE 6

The flour in Example 1 was used to prepare pasta. For this purpose the flour was mixed with a sufficient quantity of water to obtain a dough suitable for forming by extrusion (approximately 20 to 30% of water). A pasta in the form of spaghetti was obtained by extrusion through suitable dies and when subsequently cooked in boiling salted water yielded organoleptic properties entirely similar to those of a pasta made with high quality durum wheat semolina.

EXAMPLE 7

The flour in Example 2 was used to prepare bread. For this purpose the flour was mixed with a sufficient quantity of water to obtain a mouldable dough, and to this a suitable quantity of bread yeast and salt were also added. The dough was then left to rise for approximately 2 hours, mixed again and finally left to stand for approximately 1 hour before being shaped and baked in an oven at approximately 220° C.

The bread obtained in this way had optimum organoleptic properties, crustiness and crumbliness.

The flours in the examples described above are virtually interchangeable and can be used in the preparation of pasta, egg pasta, bread, bread sticks, biscottes, sweet and savoury flans, biscuits, etc., following the addition of suitable additional ingredients.

The only differences which can be found between the various flours lie in their different carbohydrate contents, which for example are lowest in the flour according to Example 1 (definitely below 5%) and tend to be higher (although always below 15%) in the flours containing fruit or vegetable fibres, on account of the residual glucide content of those fibres.

As a consequence a person who wishes to lose weight by following the method according to this invention should initially use flours such as those in Examples 1 or 2, which guarantee an absolutely negligible glucide content.

Once the ideal weight has been gained the individual can alternate the use of the abovementioned flours with those of flours (such as those in Examples 3 and 4) which have a certain, though low, glucide content due to the fruit or vegetable fibre content.

Once the individual's weight and form have become stabilized, then flours containing other ingredients such as milk proteins, dried meat or fish animal proteins, powdered milk, powdered cream, whole eggs or dried albumin or dried egg yolk only can also be introduced into the diet.

In this latter stage the carbohydrate content should however always be maintained below 20% by weight.

It should be pointed out that the flours according to the invention constitute the basis of the food intake of an individual who intends to improve his appearance by eliminating excess kilos using the method according to this invention. Provided that all carbohydrate-based foods are replaced by similar foods prepared using the flours according to the invention the individual can nevertheless consume a variety of foods rich in proteins and/or lipids (meat, fish, delicatessen products, cheeses) without any limit on quantity and without in any way prejudicing the result achieved, or losing excessive weight.

This constitutes an enormous advantage in comparison with the low-calorie diet regimes proposed hitherto, which presuppose a considerable propensity to "sacrifice" on the part of individuals who subject themselves to them, and which for this reason have therefore as a result achieved very low compliance on the part of such individuals.

In addition to imposing no quantitative limits on food intake, the method according to the invention makes it possible to vary foods consumed with great freedom, which further increases the willingness of individuals to follow the proposed diet regime satisfactorily.

The following examples relate to pharmaceutical compositions according to the present invention. The following compositions are preferably prepared in the form of a gelatine capsule.

EXAMPLE 8

Preparation of a gelatine capsule. The following components are admixed, optionally with suitable excipients to reach the capacity of the capsule: the capsule is then filled and sealed.

| Diethylpropione chlorohydrate | mg. | 20 |
|---|---|---|
| Fenfluramine | mg. | 4 |
| Benfluorex | mg. | 50 |
| Triiadiotiracetic acid | mg. | 0.4 |
| Pancreatine IX F.U. | mg. | 120 |
| Metformine | mg. | 200 |
| Na dehydrocolate | mg. | 40 |

EXAMPLE 9

Preparation of two capsules A and B which are part of a kit and which comprise different components to take in combination.

| Capsule A | | |
|---|---|---|
| Fenfluoramine | mg. | 4 |
| Benfluorex | mg. | 50 |
| Capsule B | | |
| Triiodiotiracetic acid | mg. | 0.8 |
| Pancreatine IX F.U. | mg. | 240 |
| Metformine | mg. | 370 |
| Na dehydrocolate | mg. | 80 |
| Dipotassium chlorazepate | mg. | 2 |

EXAMPLE 10

Preparation of a capsule A and a capsule B which are part of a kit and which comprise different compounds to take in combination.

| Capsule A | | |
|---|---|---|
| Diethylpropione chlorohydrate | mg. | 35 |
| Bentluorex | mg. | 150 |
| Vit. C | mg. | 100 |
| Vit. E | mg. | 100 |
| Vit. B6 | mg. | 50 |
| Capsule B | | |
| Pancreatine IX F.U. | mg. | 240 |
| Metformine | mg. | 370 |
| Na dehydrocolate | mg. | 80 |
| Dipotassium chlorazepate | mg. | 4 |

I claim:

1. A dietary weight loss method, said method comprising the step of; substantially reducing or eliminating from a person's diet all carbohydrate-based foods and replacing said carbohydrate-based foods with foods obtained using a food composition in the form of a flour substantially comprised of, as a percentage of weight, at least 50% protein, up to 20% of carbohydrates and from 30–50% of plant fibers.

2. A dietary weight loss method as claimed in claim 1, further comprising the step of administration of at least one diet adjuvant selected from the group consisting of a sedative-ansiolytic agent, an anorectic agent and a lipolytic agent.

3. A dietary weight loss method as claimed in claim 2, wherein said sedative-ansiolytic agent is a benzodiazapine, said anorectic agent is selected from the group consisting of diethylpropione chlorohydrate, fenfluramine chlorohydrate, and D-fenfluramine chlorohydrate; said lipolytic agent is selected from the group consisting of analogues of tiroxine.

4. A dietary weight loss method as claimed in claim 3, wherein said benzodiazapine is dipotassium chlorazepate.

5. A dietary weight loss method as claimed in claim 3, wherein said analogue of tiroxine is triiodiotiroacteic acid.

6. A dietary weight loss method as claimed in claim 1, further comprising the step of administration of a pharmaceutical composition comprising: a hypocholesterolemic agent; a hypotriglyceride agent; a lipasic agent; a hypoglycemic agent; and hydrocoleretic agent.

7. A dietary weight loss method as claimed in claim 6, wherein said hypocholesterolemic agent is selected from the group consisting of benfluorex and ursodesoxycolic acid.

8. A dietary weight loss method as claimed in claim 6, wherein said hypotriglyceride agent is benfluorex.

9. A dietary weight loss method as claimed in claim 6, wherein said lipasic agent is pancreatine IX F.U.

10. A dietary weight loss method as claimed in claim 6, wherein said hypoglycemic agent is metformine.

11. A dietary weight loss method as claimed in claim 6, wherein said hydrocoleretic agent is selected from the group consisting of Na dehydrocloate and ursodesoxycolic acid.

12. A dietary weight loss method as claimed in claim 1, wherein said proteins, are selected from the group comprising: gluten, soya proteins, milk proteins, soya milk proteins without lactose, dried meat proteins, dried fish proteins, smoked fish proteins, powdered egg albumin and yolk protein, wheat protein, wheat germ, rice germ, soy bean protein, and pea protein.

13. A dietary weight loss method as claimed in claim 1, wherein said plant fibers are selected from the group comprising: fibers of wheat cereals, fibers of maize cereals, fibers of oat cereals, fibers of soya cereals, tomato fibers, spinach fibers, inulin fibers, acacia fibers, orange fibers, apple fibers, fruit fibers and vegetable fibers.

14. A dietary weight loss method as claimed in claim 1, wherein said food composition further comprises fat selected from the group comprised of coconut fat, soya bean fat, egg yolk fat, cream fat and whole milk fat.

15. A dietary weight loss method as claimed in claim 1, wherein said food composition further comprises flour selected from the group comprised of tender wheat and drum wheat.

16. A dietary weight loss method, said method comprising the step of substantially reducing or eliminating from a person's diet all carbohydrate-based foods and replacing said carbohydrate-based foods with foods obtained using a food composition in the form of a flour substantially comprised of, as percentage of weight, at least 50% protein, up to 15% of carbohydrates and from 30–50% of plant fibers.

17. A dietary weight loss method as claimed in claim 16, wherein said step of substantially reducing or eliminating from said person's diet all carbohydrate-based foods and replacing said carbohydrate-based foods with said food composition in the form of a flour where said flour is substantially comprised of, as percentage of weight, up to 5% carbohydrates.

18. A dietary weight loss method as claimed in claim 17, further comprising the step of administration of at least one diet adjuvant selected from the group consisting of a sedative-ansiolytic agent, an anorectic agent and a lipolytic agent.

19. A dietary weight loss method as claimed in claim 18, wherein said sedative-ansiolytic agent is a benzodiazapine, said anorectic agent is selected from the group consisting of diethylpropione chlorohydrate, fenfluramine chlorohydrate, and D-fenfluramine chlorohydrate; said lipolytic agent is selected from the group consisting of analogues of tiroxine.

20. A dietary weight loss method as claimed in claim 19, wherein said benzodiazapine is dipotassium chlorazepate.

21. A dietary weight loss method as claimed in claim 19, wherein said analogue of tiroxine is triiodiotiroacteic acid.

22. A dietary weight loss method as claimed in claim 16, further comprising the step of administration of at least one diet adjuvant selected from the group consisting of a sedative-ansiolytic agent, an anorectic agent and a lipolytic agent.

23. A dietary weight loss method as claimed in claim 22, wherein said sedative-ansiolytic agent is a benzodiazapine, said anorectic agent is selected from the group consisting of diethylpropione chlorohydrate, fenfluramine chlorohydrate, and D-fenfluramine chlorohydrate; said lipolytic agent is selected from the group consisting of analogues of tiroxine.

24. A dietary weight loss method as claimed in claim 23, wherein said benzodiazapine is dipotassium chlorazepate.

25. A dietary weight loss method as claimed in claim 23, wherein said analogue of tiroxine is triiodiotiroacteic acid.

26. A dietary weight loss method as claimed in claim 17, further comprising the step of administration of a pharmaceutical composition comprising: a hypocholesterolemic agent; a hypotriglyceride agent; a lipasic agent; a hypoglycemic agent; and hydrocoleretic agent.

27. A dietary weight loss method as claimed in claim 26, wherein said hypocholesterolemic agent is selected from the group consisting of benfluorex and ursodesoxycolic acid.

28. A dietary weight loss method as claimed in claim 26, wherein said hypotriglyceride agent is benfluorex.

29. A dietary weight loss method as claimed in claim 26, wherein said lipasic agent is pancreatine IX F.U.

30. A dietary weight loss method as claimed in claim 26, wherein said hypoglycemic agent is metformine.

31. A dietary weight loss method as claimed in claim 26, wherein said hydrocoleretic agent is selected from the group consisting of Na dehydrocloate and ursodesoxycolic acid.

32. A dietary weight loss method as claimed in claim 16, further comprising the step of administration of a pharmaceutical composition comprising: a hypocholesterolemic agent; a hypotriglyceride agent; a lipasic agent; a hypoglycemic agent; and hydrocoleretic agent.

33. A dietary weight loss method as claimed in claim 32, wherein said hypocholesterolemic agent is selected from the group consisting of benfluorex and ursodesoxycolic acid.

34. A dietary weight loss method as claimed in claim 32, wherein said hypotriglyceride agent is benfluorex.

35. A dietary weight loss method as claimed in claim 32, wherein said lipasic agent is pancreatine IX F.U.

36. A dietary weight loss method as claimed in claim 32, wherein said hypoglycemic agent is metformine.

37. A dietary weight loss method as claimed in claim 32, wherein said hydrocoleretic agent is selected from the group consisting of Na dehydrocloate and ursodesoxycolic acid.

38. A dietary weight loss method, said method comprising the step of elimination from the a person's diet of all carbohydrate-based foods and further said method comprising the steps of:

an initial stage in which carbohydrate-based foods are replaced with a first food composition obtained using a food composition in the form of a flour substantially comprised of, as percentage of weight, at least 50% protein, up to 5% of carbohydrates and from 30–50% of plant fibers;

an intermediate stage in which said carbohydrate-based foods are replaced with a second food composition obtained using a food composition in the form of a flour substantially comprised of, as percentage of weight, at least 50% protein, up to 15% of carbohydrates and from 30–50% of plant fibers; and a maintenance stage in which said carbohydrate-based foods are replaced with a third food composition obtained using a food composition in the form of a flour substantially comprised of, as percentage of weight, at least 50% protein, up to 20% of carbohydrates and from 30–50% of plant fibers such that when said person reaches a desired weight as a result of said initial stage and said intermediate stage, said person remains on said maintenance stage to prevent recovery of lost weight, so that following said weight loss method results in sustained weight loss.

* * * * *